United States Patent
Briere et al.

(10) Patent No.: US 9,701,608 B2
(45) Date of Patent: Jul. 11, 2017

(54) PROCESS FOR THE SYNTHESIS OF 7-METHOXY-NAPHTHALENE-1-CARBALDEHYDE AND APPLICATION IN THE SYNTHESIS OF AGOMELATINE

(71) Applicant: LES LABORATOIRES SERVIER, Suresnes (FR)

(72) Inventors: Jean-François Briere, Amfreville-la-mi-Voie (FR); Raphaël Lebeuf, Lille (FR); Vincent Levacher, Fontaine-Sous-Preaux (FR); Christophe Hardouin, Sainte Adresse (FR); Jean-Pierre Lecouve, Le Havre (FR)

(73) Assignee: LES LABORATORIES SERVIER, Suresnes (FR)

( * ) Notice: Subject to any disclaimer, the term of this patent is extended or adjusted under 35 U.S.C. 154(b) by 0 days.

(21) Appl. No.: 15/101,120

(22) PCT Filed: Dec. 4, 2014

(86) PCT No.: PCT/FR2014/053159
§ 371 (c)(1),
(2) Date: Jun. 2, 2016

(87) PCT Pub. No.: WO2015/082849
PCT Pub. Date: Jun. 11, 2015

(65) Prior Publication Data
US 2016/0304429 A1   Oct. 20, 2016

(30) Foreign Application Priority Data

Dec. 5, 2013 (FR) .................... 13 62200

(51) Int. Cl.
| C07C 45/45 | (2006.01) |
| C07C 47/00 | (2006.01) |
| C07C 303/28 | (2006.01) |
| C07C 45/65 | (2006.01) |

(52) U.S. Cl.
CPC .............. *C07C 45/65* (2013.01); *C07C 45/45* (2013.01); *C07C 303/28* (2013.01)

(58) Field of Classification Search
CPC ........ C07C 45/45; C07C 45/65; C07C 47/575; C07C 303/28
See application file for complete search history.

(56) References Cited

U.S. PATENT DOCUMENTS 8,217,032 B2 * 7/2012 Dally .................. C07D 221/18
514/217.03

FOREIGN PATENT DOCUMENTS

FR 2918369 1/2009

OTHER PUBLICATIONS

Garigipati, et al., Bioorganic and Medicinal Chemistry Letters, vol. 7, No. 11, p. 1421-1426, Jun. 3, 1997.
International Search Report with Written Opinion for PCT/FR2014/053159 of Oct. 6, 2015.
Kandagatla, et al., Tetrahedron Letters, vol. 53, p. 7125-7127, Oct. 26, 2012.
International Preliminary Report for PCT/FR2014/053159 on Sep. 6, 2016.

* cited by examiner

*Primary Examiner* — Sikarl Witherspoon
(74) *Attorney, Agent, or Firm* — Hueschen and Sage

(57) ABSTRACT

Process for the industrial synthesis of the compound of formula (I):

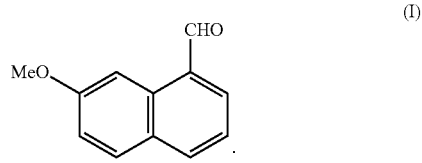

22 Claims, No Drawings

PROCESS FOR THE SYNTHESIS OF 7-METHOXY-NAPHTHALENE-1-CARBALDEHYDE AND APPLICATION IN THE SYNTHESIS OF AGOMELATINE

The present invention relates to a new process for the industrial synthesis of (7-methoxy-1-naphthalene-1-carbaldehyde and to its application in the industrial production of agomelatine, or N-[2-(7-methoxy-1-naphthyl)ethyl]acetamide.

More specifically, the present invention relates to a process for the industrial synthesis of the compound of formula (I):

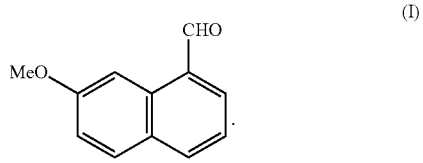 [SMILES: COc1ccc2cccc(C=O)c2c1]

The compound of formula (I) obtained according to the process of the invention is useful in the synthesis of agomelatine, or N-[2-(7-methoxy-1-naphthyl)ethyl]acetamide, of formula (II):

Agomelatine, or N-[2-(7-methoxy-1-naphthyl)ethyl]acetamide, has valuable pharmacological properties.

It does, in fact, have the double characteristic of being, on the one hand, an agonist of receptors of the melatoninergic system and, on the other hand, an antagonist of the 5-$HT_{2C}$ receptor. These properties provide it with activity in the central nervous system and, more especially, in the treatment of major depression, seasonal affective disorder, sleep disorders, cardiovascular pathologies, pathologies of the digestive system, insomnia and fatigue due to jet-lag, appetite disorders and obesity.

Agomelatine, its preparation and its use in therapeutics have been described in European Patent specifications EP 0 447 285 and EP 1 564 202.

In view of the pharmaceutical value of this compound, it is important to be able to obtain it by an effective synthesis process that is readily transferable to the industrial scale and that results in agomelatine in a good yield and with excellent purity, starting from economical and readily obtainable starting materials.

Patent specification EP 0 447 285 describes obtaining agomelatine in eight steps starting from 7-methoxy-1-tetralone. When transferred to the industrial scale, however, difficulties in implementing that process rapidy came to light.

The literature describes obtaining 7-methoxy-naphthalene-1-carbaldehyde in 5 steps starting from 8-amino-naphthalen-2-ol (Kandagatla et al., *Tetrahedron Lett.* 2012, 53, 7125-7127). The preparation of 7-methoxy-naphthalene-1-carbaldehyde in 4 steps starting from 7-methoxy-tetralone has also been described (Garipati et al., *Bioorg. Med. Chem. Lett.* 1997, 7, 1421-1426). 7-Methoxy-1-tetralone and 8-amino-naphthalen-2-ol are, however, costly starting materials and consequently the search for new synthesis routes, especially starting from less expensive reagents, is still ongoing.

The Applicant has continued his investigations and has developed a new industrial synthesis which, in reproducible manner and without the need for laborious purification, yields agomelatine with a purity which is compatible with its use as a pharmaceutical active ingredient, starting from a less costly and more readily obtainable starting material.

More especially, the Applicant has now developed a new industrial synthesis process making it possible to obtain 7-methoxy-naphthalene-1-carbaldehyde in reproducible manner without the need for laborious purification, using 7-methoxy-naphthalen-2-ol as starting material. This new starting material has the advantage of being simple and readily obtainable in large amounts at less cost. 7-Methoxy-naphthalen-2-ol also has the advantage of having in its structure a naphthalene ring system, which avoids incorporating an aromatisation step in the synthesis—a step which is always problematic from an industrial point of view.

More specifically, the present invention relates to a process for the industrial synthesis of the compound of formula (I):

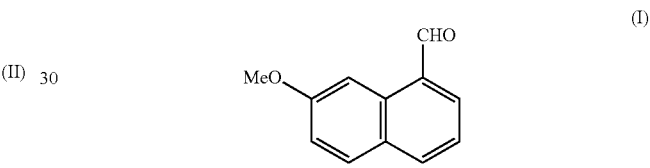

characterised in that 7-methoxy-naphthalen-2-ol of formula (III):

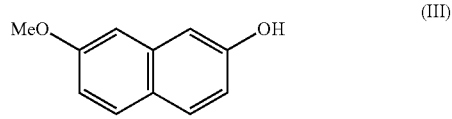 [SMILES: COc1ccc2ccc(O)cc2c1]

is used for reaction, a formylation reaction being carried out at position 1 of the compound of formula (III) to yield the compound of formula (IV):

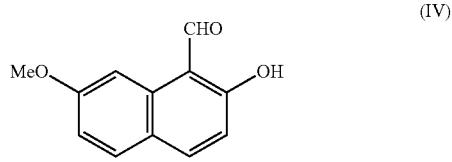 [SMILES: COc1ccc2ccc(O)c(C=O)c2c1]

which compound of formula (IV) is subjected to a sulphonylation reaction to yield the compound of formula (V):

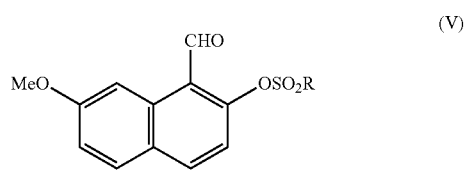

wherein R represents a —CH₃, —(CH₂)₂—CH₃, —CF₃ or tolyl group;

which compound of formula (V) undergoes a deoxygenation reaction in the presence of a transition metal and a reducing agent to yield the compound of formula (I), which is isolated in the form of a solid.

The compound of formula (III) is commercially available or readily obtainable by the skilled person using chemical reactions that are customary or described in the literature.

R preferably represents a —CH₃ or tolyl group.

In the process according to the invention, conversion of the compound of formula (III) into the compound of formula (IV) consists of the action of ethyl orthoformate in the presence of aniline followed by hydrolysis of the intermediate imine obtained.

In the process according to the invention, conversion of the compound of formula (IV) into the compound of formula (V) consists of a sulphonylation step carried out by means of the action of a sulphonyl chloride, a sulphonic anhydride or a sulphonimide. In a preferred embodiment, this sulphonylation step is carried out by means of the action of a sulphonyl chloride and, especially, tosyl chloride or mesyl chloride.

In the process according to the invention, conversion of the compound of formula (V) into the compound of formula (I) consists of a deoxygenation step in the presence of a transition metal and a reducing agent.

Preferably, the transition metal is nickel, palladium or platinum. The transition metal can be either in the form of a salt or in the form of a simple substance. Preferably, the transition metal salt is a nickel salt or a palladium salt, more preferably a palladium salt.

Advantageously, the reducing agent is either a hydride such as sodium borohydride or lithium aluminium hydride; or an aminoborane such as dimethylamine borane; or an alkoxysilane such as dimethoxymethylsilane; or an alkylsilane such as triethylsilane; or an alkaline earth metal such as magnesium; or dihydrogen. Preferably, the reducing agent is dihydrogen which is used directly in its gaseous form or is indirectly obtained by decomposition of an ammonium formate. The reducing agent is preferably dihydrogen obtained by decomposition of an ammonium formate.

In accordance with another preferred embodiment, conversion of the compound of formula (V) into the compound of formula (I) consists of a deoxygenation step in the presence of nickel, especially a nickel salt, and a hydride, preferably sodium borohydride.

In accordance with another preferred embodiment, conversion of the compound of formula (V) into the compound of formula (I) consists of a deoxygenation step in the presence of palladium and dihydrogen.

In accordance with another preferred embodiment, conversion of the compound of formula (V) into the compound of formula (I) consists of a deoxygenation step in the presence of palladium and an alkaline earth metal, preferably magnesium.

Advantageously, the reaction converting the compound of formula (V) into the compound of formula (I) is carried out in dimethylformamide, dioxane, tetrahydrofuran and toluene, and more preferably dimethylformamide.

Preferably, the reaction converting the compound of formula (V) into the compound of formula (I) is carried out between 25° C. and 110° C., more especially between 40° C. and 95° C.

In accordance with another preferred embodiment, conversion of the compound of formula (V) into the compound of formula (I) consists of a deoxygenation step in the presence of a transition metal, a reducing agent and a ligand.

The ligand can be either a phosphine ligand or a diaminocarbene ligand, more preferably a phosphine ligand and, more specifically, 1,3-bis(diphenylphosphino)propane or (9,9-dimethyl-9H-xanthene-4,5-diyl)bis(diphenylphosphane).

A variant which is advantageous for the industrial synthesis process consists of conversion of the compound of formula (IV) being carried out to form the compound of formula (I) directly, said sulphonylation reaction and said deoxygenation reaction in the presence of a transition metal being carried out as a "one-pot" procedure.

This process is especially advantageous for the following reasons:
  it makes it possible to obtain the compound of formula (I) on the industrial scale in good yields starting from a simple and low-cost starting material;
  it makes it possible to avoid an aromatisation reaction because the naphthalene ring system is present in the starting substrate;
  it makes it possible to obtain agomelatine starting from 7-methoxy-naphthalen-2-ol in a reduced number of steps.

The compounds of formula (V) obtained in accordance with the process of the invention are new and useful as intermediates in the synthesis of agomelatine and the compound of formula (I).

Preferred compounds of formula (V) are the following:
  1-formyl-7-methoxynaphthalen-2-yl 4-methylbenzenesulphonate;
  1-formyl-7-methoxynaphthalen-2-yl methanesulphonate.

The compound of formula (I) hereby obtained is subsequently subjected to a series of customary chemical reactions (for example: reduction of the aldehyde into a primary alcohol, cyanation, reduction and acetylation of the primary amine obtained) to yield agomelatine of formula (II).

The Examples hereinbelow illustrate the invention but do not limit it in any way. In order to properly validate the reaction routes, the synthesis intermediates were systematically isolated and characterised. However, it is possible to considerably optimise the procedures by limiting the number of intermediates isolated.

The structures of the compounds described were confirmed by the usual spectroscopic techniques: proton NMR (s=singlet; d=doublet; dd=doublet of doublets); carbon NMR (s=singlet; d=doublet; q=quadruplet).

EXAMPLE 1:
7-METHOXYNAPHTHALENE-1-CARBALDEHYDE

Step A:
2-hydroxy-7-methoxynaphthalene-1-carbaldehyde

7-Methoxy-naphthalen-2-ol (3.5 g; 20.11 mmol), ethyl orthoformate (3.51 mL; 21.12 mmol) and aniline (1.83 mL; 20.11 mmol) are introduced into a flask equipped with a condenser. After stirring for 20 hours at reflux and cooling, the solid is ground in a 2M ethanolic solution of hydrochloric acid (20 mL). After stirring for 30 minutes at 60° C. and cooling, the solid is collected by filtration and then washed with water and dried by azeotropic distillation with ethanol and used directly without any other purification (2.95 g; 73%).

$^1$H NMR spectroscopic analysis (CDCl₃, δ in ppm): 13.17 (s, 1H); 10.74 (s, 1H); 7.88 (d, J=9.1 Hz, 1H); 7.69 (d, J=8.9

Hz, 1H); 7.65 (d, J=2.4 Hz, 1H); 7.07 (dd, J=8.9 and 2.4 Hz, 1H); 6.97 (d, J=9.1 Hz, 1H); 3.95 (s, 3H).

Step B: 1-formyl-7-methoxynaphthalen-2-yl 4-methylbenzenesulphonate

To a solution of the product of Step A above (1 g; 4.95 mmol) in dichloromethane (20 mL) there are added triethylamine (826 µL; 5.94 mmol) and tosyl chloride (0.99 g; 5.2 mmol). After stirring for 24 hours, the solvent is evaporated off and then the residue is taken up in a mixture of water/ ethyl acetate. The organic phase is washed with a dilute solution of hydrochloric acid, water and brine, and then dried over sodium sulphate and filtered. Evaporating off the solvents results in a crude product, which is purified by recrystallised from hot ethyl acetate to yield the title product (1.132 g; 65%).

Melting point: 147-148° C.

$^{1}$H NMR spectroscopic analysis (CDCl$_3$, δ in ppm): 10.41 (s, 1H); 8.68 (d, J=2.6 Hz, 1H); 7.95 (d, J=8.9 Hz, 1H); 7.74 (d, J=8.2 Hz, 2H); 7.72 (d, J=8.9 Hz, 1H); 7.33 (d, J=8.2 Hz, 2H); 7.19 (dd, J=8.9 and 2.6 Hz, 1H); 7.15 (d, J=8.9 Hz, 1H); 3.93 (s, 3H); 2.45 (s, 3H).

$^{13}$C NMR spectroscopic analysis (CDCl$_3$, δ in ppm): 190.3 (d); 161.5 (s); 154.3 (s); 146.4 (s); 136.4 (d); 132.8 (s); 131.5 (s); 130.3 (2×d); 129.9 (d); 128.6 (2×d); 127.8 (s); 121.5 (s); 120.1 (d); 118.6 (d); 104.1 (d); 55.6 (q); 21.9 (q).

Step C: 7-methoxynaphthalene-1-carbaldehyde

The product of Step B above (356 mg; 1 mmol), palladium acetate (4.5 mg; 0.02 mmol), 1,3-bis(diphenylphosphino)propane (8.2 mg; 0.02 mmol), dimethylformamide (2 mL), triethylamine (556 µL; 4 mmol) and formic acid (150 µL; 4 mmol) are introduced into a flask placed in an oven and purged with argon. The flask is placed in a bath heated to 90° C. for 1.5 hours. After cooling, the mixture is diluted with ethyl acetate and the organic phase is washed with 1M aqueous hydrochloric acid solution and with brine, dried over sodium sulphate and filtered. After evaporating off the solvent, the crude product is purified by filtration over neutral alumina to yield the title product (139 mg; 75%).

Melting point: 65-67° C.

$^{1}$H NMR spectroscopic analysis (CDCl$_3$, 300.13 MHz, δ in ppm): 10.29 (s, 1H); 8.75 (d, J=2.6 Hz, 1H); 7.99 (d, J=8.1 Hz, 1H); 7.9 (d, J=7.1 Hz, 1H); 7.77 (d, J=8.9 Hz, 1H); 7.45 (dd, J=8.1 and 7.1 Hz, 1H); 7.23 (dd, J=8.9 and 2.6 Hz, 1H); 3.98 (s, 3H).

$^{13}$C NMR spectroscopic analysis (CDCl$_3$, 75.5 MHz, δ in ppm): 194.1 (d); 160.7 (s); 138.3 (d); 135.1 (d); 132.2 (s); 130.2 (s); 129.9 (d); 129.3 (s); 122.5 (d); 119.8 (d); 103.6 (d); 55.6 (q).

EXAMPLE 2:
7-METHOXYNAPHTHALENE-1-CARBALDEHYDE

Step A: 1-formyl-7-methoxynaphthalen-2-yl methanesulphonate

To a solution of the compound obtained in Step A of Example 1 (300 mg; 1.485 mmol) in dichloromethane (5 mL) there are added triethylamine (250 µL; 1.782 mmol) and mesyl chloride (120 µL). After stirring for one hour, the solvent is evaporated off and the residue is taken up in a mixture of ethyl acetate/water. The organic fraction is washed twice with water and then with brine, dried over sodium sulphate and filtered. Evaporating off the solvent yields the clean title product (416 mg; 95%) without the need for purification.

$^{1}$H NMR spectroscopic analysis (CDCl$_3$, δ in ppm): 10.74 (s, 1H); 8.72 (d, J=2.4 Hz, 1H); 8.03 (d, J=8.9 Hz, 1H); 7.75 (d, J=8.9 Hz, 1H); 7.36 (d, J=8.9 Hz, 1H); 7.22 (dd, J=8.9 and 2.4 Hz, 1H); 3.97 (s, 3H); 3.32 (s, 3H).

$^{13}$C NMR spectroscopic analysis (CDCl$_3$, δ in ppm): 190.4 (d); 161.6 (s); 153.2 (s); 136.8 (d); 133.1 (s); 130.0 (d); 128.0 (s); 121.6 (s); 120.3 (d); 118.2 (d); 104.0 (d); 55.7 (q); 38.5 (q).

Step B: 7-methoxynaphthalene-1-carbaldehyde

The title product (84%) is obtained in accordance with the process described in Step C of Example 1 starting from the product of Step A above and with a reaction time of 4 hours at 90° C. instead of 1.5 hours.

Melting point: 65-67° C.

$^{1}$H NMR spectroscopic analysis (CDCl$_3$, 300.13 MHz, δ in ppm): 10.29 (s, 1H); 8.75 (d, J=2.6 Hz, 1H); 7.99 (d, J=8.1 Hz, 1H); 7.9 (d, J=7.1 Hz, 1H); 7.77 (d, J=8.9 Hz, 1H); 7.45 (dd, J=8.1 and 7.1 Hz, 1H); 7.23 (dd, J=8.9 and 2.6 Hz, 1H); 3.98 (s, 3H).

$^{13}$C NMR spectroscopic analysis (CDCl$_3$, 75.5 MHz, δ in ppm): 194.1 (d); 160.7 (s); 138.3 (d); 135.1 (d); 132.2 (s); 130.2 (s); 129.9 (d); 129.3 (s); 122.5 (d); 119.8 (d); 103.6 (d); 55.6 (q).

EXAMPLE 3:
7-METHOXYNAPHTHALENE-1-CARBALDEHYDE

Sodium hydride (60%; 17 mg; 0.415 mmol) is added, in several portions, to a solution of 7-methoxy-naphthalen-2-ol (70 mg; 0.35 mmol) in anhydrous dimethylformamide (1 mL) in a flask purged with argon. After stirring for 30 minutes at ambient temperature, tosyl chloride is then added in several portions (190.5 mg; 0.36 mmol). After stirring for 4 hours at ambient temperature, 1,3-bis(diphenylphosphino) propane (7.1 mg; 0.017 mmol), palladium acetate (3.9 mg; 0.073 mmol), triethylamine (192 µL; 1.38 mmol) and formic acid (150 µL; 4 mmol) are added and the reaction mixture is heated at 90° C. for 1.5 hours. After cooling, the mixture is diluted with ethyl acetate and the organic phase is washed with 1M aqueous hydrochloric acid solution and then with brine, dried over sodium sulphate and filtered. After evaporating off the solvent, the crude product is filtered over neutral alumina (eluant: ethyl acetate) to yield the title product (61.6 mg; 95%).

Melting point: 65-67° C.

The invention claimed is:
1. A process for the synthesis of a compound of formula (I):

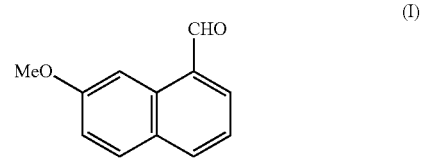 [SMILES: COc1ccc2cccc(C=O)c2c1]

wherein 7-methoxy-naphthalen-2-ol of formula (III):

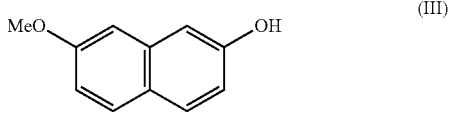 [SMILES: COc1ccc2ccc(O)cc2c1]

is used for reaction, the formyl group being introduced at position 1 to yield a compound of formula (IV):

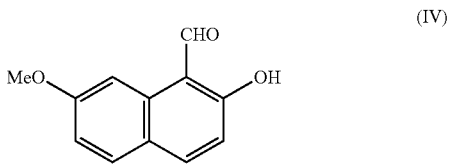

which compound of formula (IV) is subjected to a sulphonylation reaction to yield a compound of formula (V):

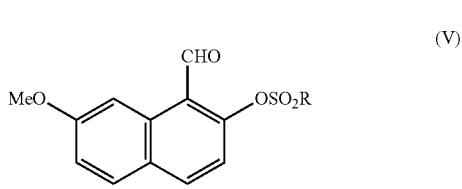

wherein R represents —CH$_3$, —(CH$_2$)$_2$—CH$_3$, —CF$_3$ or tolyl;
which compound of formula (V) undergoes a deoxygenation reaction in the presence of a transition metal and a reducing agent to yield the compound of formula (I), which is isolated in the form of a solid.

2. The process according to claim 1, wherein R represents —CH$_3$ or tolyl.

3. The process according to claim 1, wherein the conversion of the compound of formula (IV) into the compound of formula (V) is carried out by means of the action of a sulphonyl chloride, a sulphonic anhydride or a sulphonimide.

4. The process according to claim 3, wherein the conversion of the compound of formula (IV) into the compound of formula (V) is carried out by means of the action of a sulphonyl chloride.

5. The process according to claim 1, wherein, in the conversion of the compound of formula (V) into the compound of formula (I), the transition metal is nickel, palladium or platinum.

6. The process according to claim 1, wherein, in the conversion of the compound of formula (V) into the compound of formula (I), the transition metal is a palladium salt.

7. The process according to claim 1, wherein the conversion of the compound of formula (V) into the compound of formula (I) is carried out in dimethylformamide, dioxane, tetrahydrofuran or toluene.

8. The process according to claim 7, wherein the conversion of the compound of formula (V) into the compound of formula (I) is carried out in dimethylformamide.

9. The process according to claim 1, wherein the conversion of the compound of formula (V) into the compound of formula (I) is carried out between 25° C. and 110° C.

10. The process according to claim 9, wherein the conversion of the compound of formula (V) into the compound of formula (I) is carried out between 40° C. and 95° C.

11. The process according to claim 1, wherein, in the conversion of the compound of formula (V) into the compound of formula (I), the reducing agent is dihydrogen.

12. The process according to claim 11, wherein the dihydrogen is obtained by decomposition of an ammonium formate.

13. The process according to claim 1, wherein the conversion of the compound of formula (V) into the compound of formula (I) is carried out in the presence of palladium and dihydrogen.

14. The process according to claim 1, wherein the conversion of the compound of formula (V) into the compound of formula (I) is carried out in the presence of (9,9-dimethyl-9H-xanthene-4,5-diyl)bis(diphenylphosphane) or 1,3-bis(diphenylphosphino)propane.

15. A compound of formula (V):

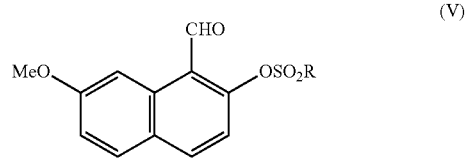

wherein R represents —(CH$_2$)$_2$—CH$_3$, —CF$_3$ or tolyl.

16. A process for the synthesis of agomelatine employing a compound of formula (V)

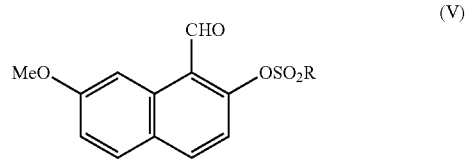

wherein R represents —CH$_3$, —(CH$_2$)$_2$—CH$_3$, —CF$_3$ or tolyl.

17. The compound according to claim 15, which is selected from the following compounds:
1-formyl-7-methoxynaphthalen-2-yl 4-methylbenzenesulphonate and
1-formyl-7-methoxynaphthalen-2-yl methanesulphonate.

18. A process for the synthesis of the compound of formula (I):

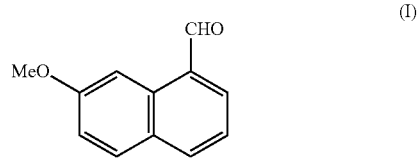 [SMILES: COc1ccc2cccc(C=O)c2c1]

employing a compound of formula (V)

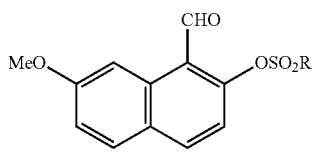

wherein R represents —CH$_3$, —(CH$_2$)$_2$—CH$_3$, —CF$_3$ or tolyl.

19. The process according to claim 18, wherein the process further comprises subjecting the compound of formula (I) to a series of reactions to provide agomelatine.

20. A process for the synthesis of a compound of formula (I)

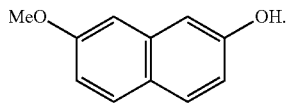

employing a compound of formula (III):

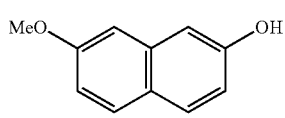

21. The process according to claim 20, wherein the process further comprises subjecting the compound of formula (I) to a series of reactions to provide agomelatine.

22. The process according to claim 16, wherein methoxynaphthalen-2-ol of formula (III):

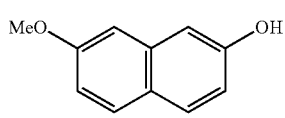

is used for reaction, and a formyl group is introduced at position 1 to yield a compound of formula (IV):

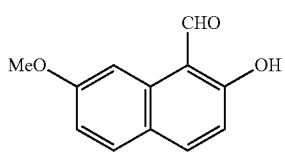

which compound of formula (IV) is subjected to a sulphonylation reaction to yield the compound of formula (V), which compound of formula (V) is subjected to a series of reactions to provide agomelatine.

* * * * *

UNITED STATES PATENT AND TRADEMARK OFFICE
CERTIFICATE OF CORRECTION

PATENT NO. : 9,701,608 B2
APPLICATION NO. : 15/101120
DATED : July 11, 2017
INVENTOR(S) : Jean-François Briere et al.

It is certified that error appears in the above-identified patent and that said Letters Patent is hereby corrected as shown below:

In the Claims

Column 8, Line 21:
"wherein R represents -$(CH_2)_2$-$CH_3$,"
Should be:
--wherein R represents $CH_3$, -$(CH_2)_2$-$CH_3$,--

Signed and Sealed this
Tenth Day of April, 2018

Andrei Iancu
*Director of the United States Patent and Trademark Office*